United States Patent [19]

Heyboer

[11] 4,207,251
[45] Jun. 10, 1980

[54] CATALYTIC OXIDATION OF FORMAMIDES TO FORM ISOCYANATES

[75] Inventor: Nico Heyboer, Wolfheze, Netherlands

[73] Assignee: Akzona Incorporated, Ashville, N.C.

[21] Appl. No.: 923,278

[22] Filed: Jul. 10, 1978

[30] Foreign Application Priority Data

Aug. 2, 1977 [NL] Netherlands .......................... 7708510

[51] Int. Cl.$^2$ .......................................... C07C 118/04
[52] U.S. Cl. ............................ 260/453 P; 260/465 D; 560/8
[58] Field of Search ...................................... 260/453 P

[56] References Cited

U.S. PATENT DOCUMENTS

| 3,099,673 | 7/1963 | Kuhle | 260/453 P |
| 3,277,140 | 10/1966 | Donovan et al. | 260/453 P |
| 3,929,859 | 12/1975 | Callahan | 260/465.8 R |
| 3,960,914 | 6/1976 | Lyons | 260/453 P |

FOREIGN PATENT DOCUMENTS 840805 10/1976 Belgium .
1152978 5/1969 United Kingdom .

OTHER PUBLICATIONS

Fu et al., et al., *J.C.S. Perkin I*, pp. 2246–2250 (1974).

*Primary Examiner*—Dolph H. Torrence
*Attorney, Agent, or Firm*—Francis W. Young; Robert F. Green; H. Walter Haeussler

[57] ABSTRACT

This invention relates to a process for preparing isocyanates from formamides wherein a formamide corresponding to the formula R–(NHCHO)$_n$, where R is an organic group and n is 1 or 2, is oxidized with an oxygen containing gas at a temperature in the range of 300° C. to 600° C. in the presence of a catalytic amount of copper and/or one or more metals of the Groups IB and VIII of the 5th and 6th period of the Periodic System of Elements to yield the corresponding isocyanate R (NCO)$_n$ where R and n have the same meaning as above, and the resultant gaseous isocyanate containing reaction mixture is subjected to a separation process to separate the product isocyanate from water of reaction.

24 Claims, 2 Drawing Figures

CATALYTIC OXIDATION OF FORMAMIDES TO FORM ISOCYANATES

BACKGROUND OF THE INVENTION

The preparation of isocyanates from formamides is known in the art. For example, U.S. Pat. No. 3,960,914 described heating a formamide corresponding to the formula R-NHCHO, where R represents an organic group, to a temperature in the range of 50° C. to 300° C. in the presence of a dehydrogenation catalyst. This process appears to result in relatively low yields, provides low selectivity and requires the continuous regeneration of large amounts of expensive catalyst.

BRIEF DESCRIPTION OF THE INVENTION

This invention relates to a process for preparing isocyanates from formamides wherein a formamide corresponding to the formula R—(NHCHO)$_n$, where R is an organic group and n is 1 or 2, is oxidized in gas phase with an oxygen containing gas in a reaction zone at a temperature between about 300° C. to about 600° C. in the presence of a catalytic amount of copper and/or one or more metals of the Groups IB and VIII of the 5th and 6th period of the Periodic System of Elements to yield the corresponding isocyanate R(NCO)$_n$ where R and n have the same meaning as above, and the resulting reaction mixture in gas phase is subjected to a separation process to separate the product isocyanate from water of reaction.

DETAILED DESCRIPTION OF THE INVENTION

Figure 1:
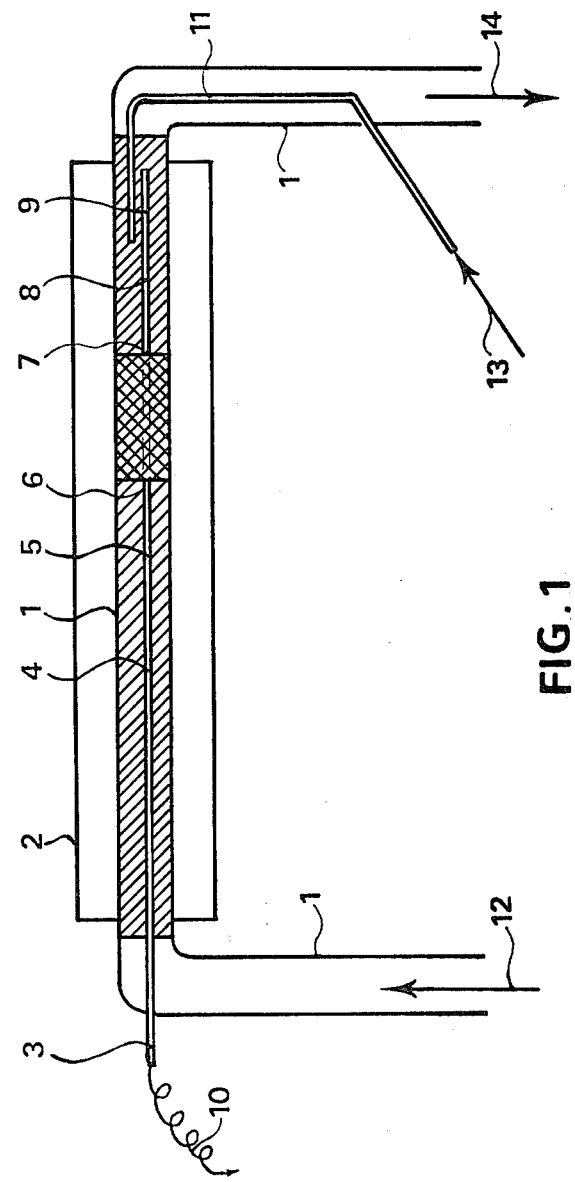
FIG. 1 is a schematic representation of the reactor employed in Examples 1 thru XXIII.

The present invention comprises a process wherein N-monosubstituted formamides corresponding to the formula

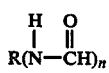

where R is an unsubstituted hydrocarbon group or substituted hydrocarbon group, generally containing not more than 24 and preferably not more than 18 carbon atoms, including substituted or unsubstituted alkyl groups, cycloalkyl groups, aryl groups, preferably phenyl, aralkyl groups or alkaryl groups, where the substituents may be, for example, chlorine, fluorine, cyanogen and alkyl carbonyl or alkoxyl carbonyl, preferably containing not more than 10 carbon atoms in the alkyl or alkoxy groups, and where n is 1 or 2, are oxidized in the gaseous phase together with an oxygen containing gas in a reaction zone at a temperature of between about 300° C. to about 600° C. in the presence of a catalytic amount of copper and/or one or more metals of the groups IB and VIII of the 5th and 6th period of the Periodic System of Elements, during a contact time of about 0.01 to about 6 seconds and preferably between about 0.1 to about 1 second to yield a corresponding isocyanate corresponding to the formula R(NCO)$_n$ where R and n are defined as above. The resultant gaseous reaction mixture is subjective to a separation process whereby the isocyanate is separated from the reactants and by-product water.

The process of the invention results in a high degree of conversion (frequently greater than 95%) with a yield of frequently more than 85% at a selectivity of often more than 90%. These results are surprising in that it could be expected that the water of reaction would rapidly combine with the product isocyanate and thus diminish or prevent the recovery of product isocyanate. It has been discovered, however, that under the prevailing gas phase reaction conditions the affinity between the isocyanate and water is so small that separation of these reaction product components in the gas phase does not present serious problems.

The process of the invention is useful with practically all N-monosubstituted formamide compounds which are gaseous under the reaction conditions, where the hydrocarbon group R, if substituted, contains substituents which do not cause any undesirable reaction or decomposition under the prevailing reaction conditions, or do not cause undue poisoning of the catalyst employed.

As to the catalyst employed in the process of the invention, while satisfactory results can be obtained with copper and all metals which are nobler than copper, it is preferred to employ one or more noble transition metals of the group: Ru, Rh, Pd, Os, Ir, Pt, Au. Optimum results have been obtained using a silver catalyst. The selectivity of the silver catalyst can be increased, if desired, by employing silver in combination with about 0.1 to about 40% by weight of the silver of a chloride, iodide or cyanide of Cu, Ru, Rh, Pd, Os, Ir or Pt.

All the above-mentioned catalytically active metals may, if desired, form part of an alloy that may in addition contain other elements which may or may not be catalytically active in themselves. Satisfactory results can also be obtained when as carrier material, for example, carborundum is used.

The use of a silver catalyst gives satisfactory results when the silver is present in the form of crystals. Optimum results are obtained when the silver catalyst is present in the form of silver wool.

The temperature at which the reaction can be satisfactorily carried out is in the range of about 300° to about 600° C. At a temperature below about 300° C. too little formamide is converted, whereas at a temperature above 600° C. side-reactions may cause the yield so much to drop that economically the process is no longer attractive. It has been found that for most N-monosubstituted formamide compounds the reaction proceeds optimally at a temperature in the range of about 350° to about 450° C. The course of the reaction is also influenced by other process conditions, such as pressure, type of catalyst, type of reactor, residence time, velocity of the gas, the ratio of formamide to oxygen, and the concentration of the formamide in the gas stream.

The proportion of formamide in the reaction mixture at the start of the reaction generally should be between 0.1 and 10 percent by volume.

Favourable results are generally obtained in the presence of at least a chemically equivalent amount of oxygen per formamide group.

The volume percentage of oxygen in the reaction mixture at the start of the reaction preferably should generally be in the range of 0.05 to 10 percent by volume. A higher percentage may not only have a detrimental effect on the yield, but it also carries with it an increased risk of flammability of the reaction mixture. Preferable results are obtained when the percentage by volume of oxygen in the reaction mixture at the start of the reaction is between 0.5 and 5 percent by volume.

The reaction generally is carried out in the presence of a substantial excess of inert gas. Consequently, the partial pressure of the gases taking part in the reaction will only be a fraction of the absolute pressure of the gas mixture. The latter pressure may vary from $<1$ kg/cm$^2$ to 10 kg/cm$^2$ or higher. For technological reasons it is most preferred that the reaction should be carried out at an absolute pressure of about 1 atmosphere.

In order to facilitate controlling the feed stock containing formamide and/or other additives, the reaction mixture may contain inert solvents which are gaseous under the reaction conditions, in addition to inert gas. Examples of these solvents include hydrocarbons such as benzene, toluene, ethyl benzene, xylene, biphenyl, n-pentane, n-hexane, n-heptane, cyclopentane, cyclohexane, methylcyclopentane, nitriles such as benzonitrile, tolunitrile and adipodinitrile; esters such as the octyl esters of acetic acid and butyric acid; 1-methylnaphthalene and tetrahydronaphthalene.

Surprisingly, it has been found that the selectivity of the reaction can be considerably improved if it is carried out in the presence of a chlorinated organic compound which is gaseous under the reaction conditions. As examples useful chlorinated organic compounds include chlorinated hydrocarbons such as methyl chloride, ethyl chloride, dichloroethane, chlorinated polyphenyl compounds, chlorinated biphenyl, o-dichlorobenzene or mixtures of these compounds.

The selectivity of the reaction can also be improved in the presence of sulphur, hydrogen sulphide and/or an organic sulphur compound containing sulphur in divalent form. An example of such an organic sulphur compound is carbon disulphide. Other examples are thioalcohols such as methane thiol, butane thiol, thio-ethers, thioacetals, thiol esters, thiophene and homologous compounds. The amount of sulfur or sulfur compound employed in the reaction mixture may vary from a few p.p.m. by volume up to as much or more than an equivalent amount by weight of the N-mono-substituted formamide compounds. Very good results are obtained when the amount of the chlorinated organic compound and/or the amount of S, H$_2$S and/or organic sulphur compound in the reaction mixture is between 1 and 100 p.p.m. by volume.

At the end of the above desired isocyanate forming reaction, rapid steps should be taken to prevent water and isocyanate from entering into reaction with each other. Several procedures can be employed to accomplish this result. In one procedure, upon termination of the reaction, the reaction mixture is very rapidly cooled, after which the water-containing phase and the isocyanate-containing phase are separated from each other as fast as possible by a known separation method, for example, a physical separation method such as filtration and/or extraction. A disadvantage to this procedure is the cost of rapid cooling. Moreover, there is always the risk of the isocyanate reacting with water where there is insufficient or insufficiently rapid cooling.

Another separation procedure comprises that, upon termination of the reaction, but prior to condensation of the isocyanate, the reaction mixture is passed over a water-absorbing agent. As examples of useful water-absorbing agents include magnesium sulphate, sodium sulphate and/or calcium chloride. As the water must be eliminated prior to or during condensation of the isocyanate, it is preferred that use should be made of a drying agent which is still satisfactorily effective at relatively high temperatures. It has been found that this last-mentioned requirement is very well satisfied by using a molecular sieve, preferably of the A3 type.

Surprisingly, it has been found that rapid cooling or drying of the reaction mixture prior to condensation of the isocyanate is not required, provided that the condensation of the isocyanate is effected in the presence of a water-immiscible or substantially water-immiscible solvent for the isocyanate. Examples of suitable solvents include benzene, toluene, xylene, chlorinated hydrocarbons such as carbon tetrachloride, trichloroethylene, ethylene dichloride and various isomers of chlorobenzene, such as 1,3-dichlorobenzene.

Depending on the temperature to which the solvent-containing reaction mixture is cooled the water formed in the reaction may or may not be condensed. If sufficient solvent is employed, and if the contact time is not unduly long, the persentage isocyanate, if any, which will decompose as a result of its reacting with water of condensation is practically negligible. If these two requirements are difficult to achieve, or if otherwise desired, this solvent borne isocyanate recovery process can be carried out in the presence of a water-absorbing agent during and/or after the condensation of the solvent/isocyanate mixture. The same water-absorbing agents may be employed as mentioned above.

An alternative process in which rapid cooling or drying of the reaction mixture, prior to condensation of the isocyanate, is no longer required, comprises passing the reaction mixture emerging from the reaction zone, optionally after having been cooled to some degree, into a water-immiscible or practically water-immiscible solvent for the isocyanate. Upon condensation, if any, of the water formed during the reaction, the water may be separated in the form of an immiscible phase. Optionally, a finely divided water-absorbing agent may be suspended in the solvent. Both the solvent and the water-absorbing agent can be the same materials as indicated above.

The solvent present during condensation of the isocyanate may be incorporated into the reaction mixture during, before or after the reaction. It may be added in a liquid or in a gaseous state. Preferably the amount of solvent employed is sufficient to absorb as much as possible of the isocyanate formed. One prefered method of adding the solvent consists in the solvent being sprayed into the reaction mixture emerging from the reaction zone.

In order to reduce or avoid the use of a water separator and/or drying agents, the temperature at which the solvent-isocyanate mixture is caused to condense or the temperature of the solvent through which the reaction mixture is passed should be so chosen that it is just above the dew point of the water contained in the reaction mixture after both the solvent and the isocyanate have been separated therefrom. In order to avoid condensation of the isocyanate before the condensation of the solvent for the isocyanate, the solvent for the isocyanate should be chosen so that its boiling point is not lower than 150° C. It is preferred that a solvent having a boiling point in the range of about 200° to about 300° C. be employed. Examples of suitable solvents include mentioned aromatic hydrocarbons such as cumene, pseudo cumene, biphenyl, α-methyl napththalene; aliphatic and cycloaliphatic hydrocarbons such as decane, hexahydrocumene, aromatic halohydrocarbons such as ortho-dichlorobenzene, bromobenzene, α-chloronaphthalene; esters such as the octyl esters of acetic acid and butyric acid; nitriles such as adipodinitrile, benzonitrile, and ketones such as benzophenone.

The gas phase oxidation reaction of the N-mono-substituted formamides to form isocyanates can be conducted in a continuous or batch operation. It is preferred, however, that the reaction be carried out continuously. Separation of the resulting reaction mixture may again be carried out continuously or batchwise. Here too, a continuous process is generally preferred.

Examples of organic isocyanates that can be prepared by the process of this invention include hexyl isocyanate, octyl isocyanate, dodecyl isocyanate, octadecyl isocyanate, tetramethylene diisocyanate, pentamethylene diisocyanate, hexamethylene diisocyanate, octamethylene diisocyanate, undecamethylene diisocyanate, dodecamethylene diisocyanate, cyclohexyl isocyanate, β-naphthyl isocyanate, xylene diisocyanate, diphenyl methane 4,4'-diisocyanate, benzyl isocyanate, phenylethyl isocyanate, phenyl isocyanate, methyl isocyanate, ethyl isocyanate, propyl isocyanate, eicosyl isocyanate, tetracosyl isocyanate, p-dodecylphenyl isocyanate, 3-chloro-4-octylphenyl isocyanate, 2,4-toluene diisocyanate, 2,6-toluene diisocyanate, and mixtures of the afore-mentioned compounds.

The following examples are given to illustrate the process of the present invention. They are, of course, not to be regarded as limiting the scope thereof.

the cross-hatched portion of the reactor contained the catalyst. A stainless steel tube 11, terminated near thermo couple 8, through which tube a high-boiling solvent 13 was passed which, upon evaporation, immediately mixed with the reaction mixture emerging from the catalyst bed. The mixture 14 consisting of the solvent 13, together with the components of the reaction mixture, was passed to a cooler. The feed stock for the reactor was a gaseous mixture 12, which had been obtained by the drop-wise charging of a liquid mixture of the formamide and another liquid, which was chemically inert to the reactants, to a carborundum-filled vertically positioned glass evaporator through which there was passed a nitrogen stream, into which a particular amount of air or oxygen had been taken up. The evaporator was heated in an oil bath to a temperature in the range of about 160° to 200° C. The condenser consisted of a glass tube filled with small glass rings and provided with a water jacket. The condensor was adjusted to cool the mixture 14° to 25° C. Under these conditions there was little or no condensation of water. The composition of the condensed mixture was analysed by gas chromatography employing a 1 m glass OV 225 column at a temperature of 100° to 250° C. For a rapid gas chromatograph determination, a liquid inert to the reactant was fed into the reactor as an internal reference, along with the formamide. In each run, the feed 12 stock was obtained by evaporating a mixture of equal amounts by weight of phenyl formamide and benzonitrile (internal reference for the chromatographic analysis) at a rate of 5 ml/hour in a gas stream consisting of nitrogen (48–120 l/hour) and air (3.5–16 l/hour). As the high-boiling isocyanate solvent 13, 1-chloronaphthalene or 1-bromonaphthalene was used (30 ml/hour). The results are given in the following table.

TABLE

| Example | Catalyst | Temp. Catalyst Bed (°C.) | Volume Percentage In Feed Stock | | Residence Time in Catalyst Bed (Seconds) | Phenyl Isocyanate Yield (%) | Selectivity (%) |
| --- | --- | --- | --- | --- | --- | --- | --- |
| | | | Oxygen | Phenyl Formamide | | | |
| I | 5% Pt on quartz wool | 380 | 2.5 | 0.9 | 2.0 | 9 | 18 |
| II | copper tape | 390 | 2.5 | 0.8 | 1.5 | 16 | 35 |
| III | Pd on glass wool | 345 | 1.0 | 0.4 | 0.4 | 6 | 9 |
| IV | Rh on glass wool | 350 | 4.1 | 0.7 | 0.5 | 8 | 14 |
| V | Ru on glass wool | 310 | 3.0 | 0.7 | 0.5 | 2 | 19 |
| VI | Ir on glass wool | 400 | 1.5 | 0.4 | 0.2 | 3 | 6 |
| VII | Ag-wool | 350 | 0.75 | 0.55 | 0.5 | 59 | 66 |
| VIII | Ag-crystals | 375 | 1.2 | 0.75 | 0.5 | 48 | 58 |
| IX | Ag on Carborundum | 345 | 0.8 | 0.4 | 0.2 | 26 | 38 |

EXAMPLES I–IX

In these examples use is made of a reactor which is schematically illustrated in FIG. 1, wherein the numeral 1 refers to a stainless steel tubular reactor 70 cm long and 2.5 cm in diameter. The tubular reactor was provided with a heating jacket 2 accomodating electric heating elements. The temperature of the reactor was kept at a pre-set value by means of two thermocouples. Tube 3, running along the center line of the tubular reactor, contained thermocouples 4, 5, 6, 7, 8 and 9, which were connected to a recorder 10. The hatched portion of the reactor was filled with carborundum and

EXAMPLE X

The procedure followed in this example was entirely in accordance with that used in the preceding examples, except that the feed stock consisting of a mixture of equal amounts by weight of n-hexyl formamide and benzonitrile. This mixture was evaporated at a rate of 5 ml/hour in a gas stream consisting of nitrogen (98 liters/hour) and air (1.2 liters/hour). The catalyst bed had a volume of 30 ml and contained 20 grams of silver wool, the filaments of which had a diameter of 0.03 mm. The temperature was 410° C. The mean residence time in the catalyst bed was 0.5 seconds. As the high-boiling solvent, 1-bromo-naphthalene, was fed to the reactor at a rate of 30 ml/hour. After a few hours the yield of n-hexyl isocyanate stabilized to 81% and the selectivity to 85%, calculated on the amount of formamide used.

EXAMPLE XI

The procedure in this example was entirely in accordance with that used in Example X, except that the starting mixture consisted of equal amounts by weight of n-hexyl formamide and benzonitrile and was evaporated at a rate of 30 ml/hour in a gas stream of nitrogen (117 liters/hour) and air (7.2 liters/hour). As the high-boiling solvent, 1-bromonaphthalene was supplied at a rate of 100 ml/hour. The mean residence time was 0.35 seconds. The yield of n-hexyl isocyanate was 85% and the selectivity 91%.

EXAMPLE XII

In accordance with the procedure described in Example XI n-hexyl formamide was evaporated at a rate of 10.5 g/hour in a gas stream of nitrogen (120 liters/hour) and air (5.5 liters/hour). As the high-boiling solvent, 1-methyl naphthalene, was used. The n-hexyl isocyanate yield was determined both by gas chromatograph (68%) and by titration with dibutylamine in accordance with the method of David and Staley in High Polymers Vol. XVI Analytical Chem. of Polyurethanes Part III (1969) 87 (Wiley Interscience). This method gave a value of 70%. The selectivity was 82%.

EXAMPLE XIII

This example was carried out entirely in accordance with Example X, except that the feed stock consisted of a mixture of equal amounts by weight of n-hexyl formamide and benzonitrile and was evaporated at a rate of 6 ml/hour. Nitrogen was fed at a rate of 100 liters/hour and air at a rate of 1.7 liters/hour. To the gas stream there was fed, in addition, 0.25% of 1,2-dichloroethane, calculated on the amount by weight of hexyl formamide. The mean residence time was 0.45 seconds. As the high-boiling solvent, 1-chloronaphthalene was charged to the reactor at a rate of 30 ml/hour. The use of a reaction temperature of 420° C. and a catalyst bed of 20 ml (20 g) of silver wool gave n-hexyl isocyanate in 67% yield at a selectivity of 97%.

EXAMPLE XIV

Using the procedure of Example X, a feed mixture of equal amounts by weight of n-hexyl formamide and benozonitrile was evaporated at a rate of 9 ml/hour in a gas stream of nitrogen (48 liters/hour) and air (2 liters/hour). This gas mixture was passed over an 8 cm-long catalyst bed of 15 grams of silver wool at a temperature of 425° C. The residence time was 0.44 seconds. The feed rate of 1-chloronaphthalene was 50 ml/hour. The condensor was set to cool the reaction mixture down to a temperature of about 0° C., which resulted in the separation in the condensor of two immiscible liquid phases. The upper phase consisted of water, the other of 1-chloronaphthalene in which n-hexyl isocyanate and non-converted n-hexyl formamide were dissolved. After separation of the two phases the amount of n-hexyl isocyanate was determined. The calculated n-hexyl isocyanate yield was 76% at a selectivity of 94%.

EXAMPLE XV

This examples was carried out entirely in accordance with the procedure described in Example XIV, except that the water was not separated, but bound with the aid of drying agents. In independent experiments with anhydrous sodium sulphate, magnesium sulphate and molecular sieve A3, respectively, results were obtained similar to those obtained in Example XIV.

EXAMPLE XVI

This example was carried out entirely in accordance with the procedure given in Example XIV, except that the small glass rings in the condenser were replaced with molecular sieve A3. It was found that both the yield and the selectivity were the same as obtained in Example XIV.

EXAMPLE XVII 9 ml per hour of a mixture of equal amounts by weight of n-hexyl formamide and benzonitrile were evaporated in a gas stream (91 liters of $N_2$ and 2 liters of air). The procedure used was entirely in accordance with that of Example XIV, except that the catalyst consisted of 5 ml (about 5 grams) of silver wool. At a temperature of 590° C. this resulted in a residence time of 0.065 seconds. As the high-boiling solvent 1-chloronaphthalene was added at a rate of 48 ml/hour. The yield of n-hexyl isocyanate was 12% at a selectivity of 28%.

EXAMPLE XVIII

The experiment of Example XVII was repeated in such a way that a catalyst bed of only 2 ml was used. The $N_2$ was fed at a rate of 106 liters per hour along with air at a rate of 2.2 liters per hour. The residence time was 0.025 seconds at 495° C. The yield of isocyanate was 32% at a selectivity of 57%.

EXAMPLE XIX

Per hour 5.16 grams of cyclohexyl formamide were evaporated in a gas stream (100 liters of $N_2$ and 5 liters of air). The starting mixture was passed over 20 ml of silver wool at a temperature of 440° C., which corresponded to a mean residence time of 0.4 seconds. The procedure was further entirely in accordance with that of Example X, except that as the high-boiling solvent, 1-chloronaphthalene was charged to the reactor at a rate of 50 ml/hour. The yield of cyclohexyl isocyanate was determined by gas chromatography and found to be 76% at a selectivity of 79%. Titration with dibutylamine in accordance with the method described in the publication of David and Staley mentioned in Example XII showed a yield of 76%.

EXAMPLE XX

The experiment was carried out entirely in accordance with the procedure given in Example XIX, except that a mixture of equal amounts by weight of n-hexyl formamide benzonitrile and o-dichlorobenzene was evaporated at a rate of 9 ml/hour in a gas stream consisting of nitrogen of (90 liters/hour) and air (9 ml/hour). The gas mixture was passed over 20 ml of silver wool at a temperature of 410° C., which corresponded to a mean residence time of 0.5 seconds. As the high-boiling solvent, 1-chloronaphthalene was charged to the reactor at a rate of 30 ml/hour. The yield of n-hexyl isocyanate was 41% at a selectivity of 72%. The o-dichlorobenzene could be recovered quantitatively.

EXAMPLE XXI

This example is entirely in accordance with Example XIX, except that use was made of a mixture of equal amounts by weight of benzyl formamide and 1-methyl naphthalene which was evaporated at a rate of 5.7 grams per hour in a gas stream of nitrogen (118 liters/hour) and air (1.4 liters/hour). The temperature of the catalyst bed was 415° C., the mean residence time 0.4 seconds. As the high-boiling solvent, 1-chloronaphthalene was charged to the reactor at a rate of 30 ml/hour. The yield of benzyl isocyanate was 57% at a selectivity of 80%.

EXAMPLE XXII

The experiment of Example X was repeated in such a way that a mixture of phenyl formamide and benzonitrile was evaporated at a rate of 5 ml/hour in a gas stream of 110 liters of nitrogen and 3 liters of air/hour. The gas mixture also comprised carbon disulphide, which was fed at a rate of 0.67% per hour, calculated on the added amount by weight of n-hexyl formamide. Use of the same catalyst bed as in Example XIX at a temperature of 375° C. resulted in a yield of phenyl isocyanate of 41% at a selectivity of 74%.

EXAMPLE XXIII

The experiment of Example XIX was repeated in such a way that a mixture of equal parts by weight of m-tolyl formamide and benzonitrile was evaporated at a rate of 5 ml/hour in a gas stream of nitrogen and air fed at rates of 118 liters and 2.8 liters per hour, respectively. 1-Chloronaphthalene was charged to the reactor at a rate of 30 ml/hour. At a temperature of 415° C. the yield of m-tolyl isocyanate was 70% and the conversion of the formamide was practically quantitative.

EXAMPLE XXIV

Figure 2:
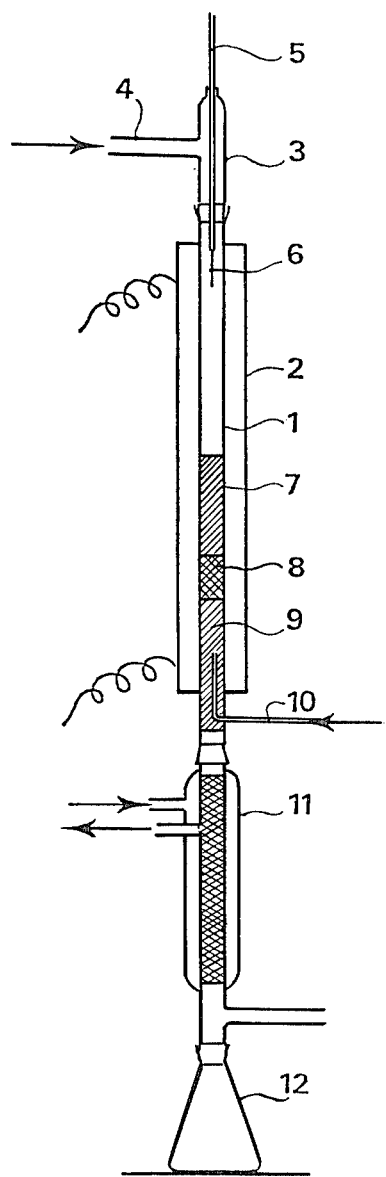
FIG. 2 is a schematic representation of the reactor employed in Examples XXIV-XXX.

In this example, as well as in the following examples, use was made of a somewhat varied set up of the reactor employed in the preceding examples. The apparatus is schematically illustrated in FIG. 2, wherein the numeral 1 refers to a stainless steel tubular reactor 70 cm long and 2 cm in diameter. The vertically positioned tubular reactor was provided with a stainless steel jacket 2 accomodating electric heating elements. Above the jacket 2 the tubular reactor ended in a space 3 to which there was connected a line 4 for the supply of the gas stream. Along the center line of the space 3, there was provided a stainless steel tube 5 which ended in a capillary tube 6. The feed stock of mono- and/or diformamide along with, if desired, some solvent was charged to the reactor through the stainless steel tube 5. The distance from the lower end of the capillary tube to the upper end of the hatched portion 7 in the tubular reactor was about 20 cm. The hatched portion 7 comprised a carborundum bed 15 cm long. The cross-hatched portion below bed 7 was the catalyst bed 8, which in the experiments described hereinafter consisted exclusively of silver wool. The hatched portion below catalyst bed 8 contained a carborundum bed 9–13 cm long. Into this bed terminated a stainless steel tube 10 through which, in all experiments, a high-boiling solvent was passed. Under the reactor 1 was a glass condensor 11 which was filled with glass beads. The low-volatility components were collected in a sampling bottle 12 and subsequently analysed by gas chromatography with a 1 m glass OV 225 column. In the following examples the mixture fed through tube 5 had already been heated to a temperature of about 100° C. The temperatures had further been so adjusted that at the end of the Capillary tube 6 the temperature was about 150° C. At the top of the carborundum bed 7 the temperature was about 300° C. with temperatures gradually increasing through the bed to the temperature of the catalyst bed 8 (about 410° to 470° C.). In the carborundum bed 9 the temperature finally decreased to about 300° C. and the exit end. Evaporation of all the liquids was realized with the aid of a gas stream added through line 4, the feed rate of which varied from 108 to 136 liters per hour for nitrogen and from 0.9 to 10 liters per hour for air. The temperature of the condenser was so set that the reaction mixture left the condenser at a temperature of approximately 25° C.

Through tube 5 there was fed a mixture of equal amounts by weight of n-octadecyl formamide and m-tolunitrile (internal reference for the gas chromatograph determination) at a rate of 9 ml/hour. This mixture was evaporated in a gas stream of nitrogen (110 liters/hour) and air (3.0 liters/hour). The amount of catalyst (silver wool) was 20 ml (20.0 grams). The temperature was 470° C. A high-boiling solvent, 1-chloronaphthalene, was fed through the tube 10 at a rate of 30 ml/hour. The yield of octadecyl isocyanate was 47%. At a conversion of 72% this corresponded to a selectivity of 65%.

EXAMPLE XXV

The procedure in this example was entirely in accordance with that of the preceding example, except that the starting material consisted of a mixture of equal amounts by weight of m-methoxy carbonylphenyl formamide and m-tolunitrile fed to the reactor at a rate of 4.5 ml/hour. This mixture was evaporated in a gas stream of nitrogen (136 liters/hour) and air (0.9 liters/hour). The temperature of the catalyst bed (15 ml) was 410° C. The residence time was 0.17 seconds. As the high-boiling solvent for the isocyanate, tetralin was added at a rate of 30 ml/hour. The yield of m-methoxycarbonylphenyl isocyanate was 53% at a selectivity of 62%.

EXAMPLE XXVI

The experiment of Example XXV was repeated in such a way that a mixture of m-cyanophenyl formamide, m-tolunitrile and benzonitrile in a weight ratio of 1:1:5 was fed to the reactor at a rate of 12 ml/hour. The mixture was evaporated in a gas stream of nitrogen (108 liters/hour) and air (1.8 liters/hour). The yield of m-cyanophenyl isocyanate was 29% at a virtually quantitative conversion.

EXAMPLE XXVII

In accordance with the procedure used in Example XXV a mixture of hexamethylene diformamide, adiponitrile (internal reference for the gas chromatograph determination) and biphenyl in a weight ratio of 1:1:5 was fed at a rate of 12 ml/hour. The gas stream consisted of nitrogen (110 liters/hour) and air (10 liters/hour). The residence time in the catalyst bed (20 ml, or about 20 grams of silver wool, the filaments of which had a diameter of 0.03 mm) was 0.25 seconds at a temperature of 430° C. As the high-boiling solvent, 1-chloronaphthalene was added at a rate of 30 ml/hour. The conversion was found to be quantitative. The yield of hexamethylene diisocyanate was 30%.

EXAMPLE XXVIII

The experiment of Example XXVII was repeated in such a way that use was made of 12 ml/hour of a mixture of decamethylene diformamide, adiponitrile (internal reference) and biphenyl in a weight ratio of 1:1:5. The conversion was again quantitative, with decamethylene diisocyanate being obtained in 31% yield.

EXAMPLE XXIX

In the same way as indicated in Example XXVII 12 ml/hour of a mixture of 2,4-toluene diformamide, benzonitrile (internal reference) and gamma-butyrolactone in a weight ratio of 1:1:5 were evaporated in a gas stream of 120 l/hour $N_2$ and 8.5 l/hour air. The residence time in the catalyst bed was 0.2 seconds at a temperature of 430° C. The conversion was quantitative and the yield of 2,4-toluene diisocyanate 27%.

EXAMPLE XXX

In the same way as indicated in Example XXVII 12 ml/hour of a mixture of m-xylylene diformamide, 1-methyl-naphthalene (internal reference) and gamma-butyrolactone in a weight ratio of 1:1:5 were evaporated in a gas stream of 112 l/hour $N_2$ and 6.0 l/hour air. The conversion was quantitative and the yield of m-xylylene diisocyanate 21%.

What is claimed is:

1. A process for preparing an isocyanate corresponding to the formula $$R(NCO)_n$$

where R is an unsubstituted alkyl group, cycloalkyl group, aryl group, aralkyl group or alkaryl group containing not more than 24 carbon atoms, or one of said groups substituted with chlorine, fluorine, cyanogen, alkyl carbonyl or alkoxy carbonyl containing not more than 10 carbon atoms in the alkyl or alkoxy group and n is 1 or 2 which (a) comprises oxidizing an N-monosubstituted formamide corresponding to the formula $$R(\underset{|}{\overset{H}{N}}-\underset{}{\overset{O}{\overset{\|}{C}}}-H)_n$$

where R and n are defined as above, in the gas phase reaction with an oxygen containing gas in a reaction zone at a temperature between about 300° C. to about 600° C. in the presence of a catalytic amount of copper and/or one or more metals of groups IB and VIII of the 5th and 6th period of the Periodic System of Elements, for a contact of about 0.01 to about 6 seconds to form said isocyanate and (b) subjecting the resultant gaseous isocyanate containing reaction mixture to a separation process to separate the product isocyanate from water of reaction.

2. The process as in claim 1, wherein the contact time is in the range of 0.1 to 1 second.

3. The process as in claims 1 or 2, wherein the oxidation reaction is carried out in the presence of a silver catalyst.

4. The process as in claim 3, wherein the silver catalyst is present in the form of silver wool.

5. The process as in claim 3, wherein the silver catalyst is present in the form of silver crystals.

6. The process as in claim 3, wherein the silver catalyst is used on carborundum as carrier material.

7. The process as in claim 1 wherein the oxidation reaction is carried out at a temperature in the range of about 350° to about 450° C.

8. The process as in claims 1 or 7 wherein at the start of the oxidation reaction the proportion of formamide in the reaction mixture is in the range of 0.1 to 10 percent by volume.

9. The process as in claims 1 or 7 wherein at least a chemical equivalent amount of oxygen is present per formamide group.

10. The process as in claims 1 or 7 wherein at the start of the reaction the proportion of oxygen in the reaction mixture is in the range of 0.05 to 10 percent by volume.

11. The process as in claim 10, wherein at the start of the reaction the proportion of oxygen in the reaction mixture is in the range of 0.5 to 5 percent by volume.

12. The process as in claim 1 wherein the reaction is carried out in the presence of a chlorinated organic compound which is gaseous under the reaction conditions.

13. The process as in claim 1 wherein the reaction is carried out in the presence of S, $H_2S$ and/or an organic sulphur compound in which the sulphur is contained in divalent form.

14. The process as in claim 12, wherein the amount of chlorinated organic compound in the reaction mixture is in the range of 1 to 100 p.p.m. by volume.

15. The process as in claim 13, wherein the amount of S, $H_2S$ and/or organic sulphur compound in the reaction mixture is in the range of 1 to 100 p.p.m. by volume.

16. The process as in claim 1 wherein upon conclusion of the reaction the reaction mixture is rapidly cooled, after which the $H_2O$-containing phase and the isocyanate-containing phase are rapidly separated from each other.

17. The process as in claim 1 wherein upon conclusion of the reaction, but prior to condensation of the isocyanate, the reaction mixture is passed over a water-absorbing agent.

18. The process as in claim 1 wherein the condensation of the isocyanate is effected in the presence of a water-immiscible or substantially water-immiscible solvent for the isocyanate.

19. The process as in claim 18 wherein during or after condensation of the isocyanate a water-absorbing agent is present.

20. The process as in claim 1, wherein the reaction mixture emerging from the reaction zone after it is passed with or without cooling into a water-immiscible or substantially water immiscible solvent for the isocyanate.

21. The process as in claim 20, wherein a finely divided water absorbing agent is suspended in the solvent.

22. The process as in claim 18, wherein the temperature at which the solvent-isocyanate mixture is condensed above the dew point of the water present in the reaction mixture after the separation therefrom of both the solvent and isocyanate.

23. The process as in claim 20, wherein the temperature of the solvent through which the reaction mixture is passed is above the dew point of the water contained in the reaction mixture after separation therefrom of both the solvent and the isocyanate.

24. The process as in claims 18, 19, 20, 21, 22, or 23 wherein the solvent for the isocyanate has a boiling point higher than the boiling point of the isocyanate.

* * * * *